United States Patent
Hanrahan et al.

(10) Patent No.: US 7,840,122 B1
(45) Date of Patent: Nov. 23, 2010

(54) MEDICINE VAPORIZER WITH CRIMPED CONDUCTIVE PINS

(75) Inventors: Kevin Patrick Hanrahan, Santa Barbara, CA (US); Damon Douglas Brink, Goleta, CA (US)

(73) Assignee: IntriMed Technologies, Inc., Oxnard, CA (US)

( * ) Notice: Subject to any disclaimer, the term of this patent is extended or adjusted under 35 U.S.C. 154(b) by 979 days.

(21) Appl. No.: 11/655,618

(22) Filed: Jan. 19, 2007

(51) Int. Cl.
*A01G 13/06* (2006.01)
(52) U.S. Cl. .................. 392/386; 392/387; 219/538; 219/541
(58) Field of Classification Search .................. None
See application file for complete search history.

(56) References Cited

U.S. PATENT DOCUMENTS

| | | | | |
|---|---|---|---|---|
| 2,535,013 A | * | 12/1950 | Freedom | 439/877 |
| 4,090,667 A | * | 5/1978 | Crimmins | 439/189 |
| 4,951,389 A | * | 8/1990 | Kaley et al. | 29/863 |
| 5,342,996 A | * | 8/1994 | Ito | 174/84 C |
| 6,071,152 A | * | 6/2000 | Achammer et al. | 439/733.1 |
| 6,312,296 B1 | * | 11/2001 | Jones | 439/751 |
| 7,513,781 B2 | * | 4/2009 | Galauner et al. | 439/70 |
| 7,537,463 B1 | * | 5/2009 | Farole et al. | 439/74 |
| 2005/0268911 A1 | | 12/2005 | Cross et al. | |
| 2007/0155255 A1 | * | 7/2007 | Galauner et al. | 439/891 |

FOREIGN PATENT DOCUMENTS

| WO | WO 94/09842 A1 | 5/1994 |
|---|---|---|
| WO | WO 03/095012 A1 | 11/2003 |

* cited by examiner

*Primary Examiner*—Thor S Campbell
(74) *Attorney, Agent, or Firm*—Joshua C. Harrison, Esq.; Barcelo, Harrison & Walker, LLP

(57) ABSTRACT

A medicine vaporizer for an inhaler includes a metal louver. The metal louver has a first end and an opposing second end, and defines a louver thickness. The medicine vaporizer also includes first and second electrically conductive pins that define a pin thickness greater than the louver thickness. The first electrically conductive pin includes a first crimping region that is attached to and crimped over the first end. The second electrically conductive pin includes a second crimping region that is attached to and crimped over the second end.

36 Claims, 3 Drawing Sheets

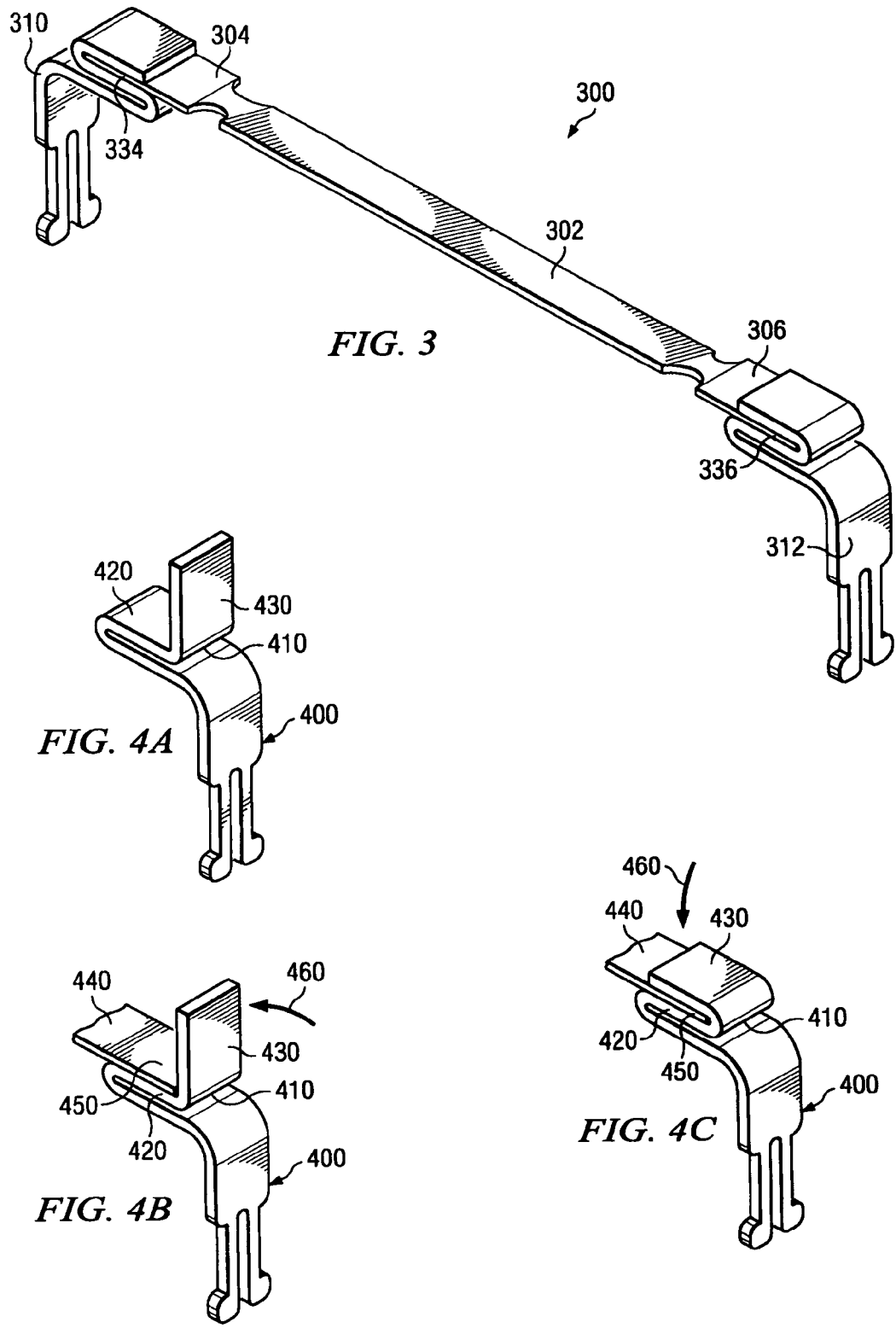

MEDICINE VAPORIZER WITH CRIMPED CONDUCTIVE PINS

FIELD OF THE INVENTION

The present invention relates generally to inhalers, and in particular to a medicine vaporizer with crimped conductive pins for an inhaler.

BACKGROUND

Medicinal inhalers can deliver a medicine or drug to the circulatory system of a patient more rapidly than ingestion (e.g. swallowing a pill) or subcutaneous injection (SCI), but typically less rapidly than intravenous injection. Medicinal inhalers are especially rapid in delivering medicines to a patient's lungs, heart, or central nervous system because blood flow from the lungs proceeds directly to the heart and from there to the brain. Moreover, the use of a medicinal inhaler is typically painless and much more convenient (for the patient) than is SCI or intravenous injection, and may reduce the risk of infection and eliminate the risks associated with improper needle disposal. For at least these reasons, inhalation has become a preferred method for patients to self-introduce certain medicines, for example bronchodilators and various psychoactive drugs.

There are several broad types of medicinal inhalers, each type distinguishable from the others by its structural and functional characteristics and by a different set of advantages and disadvantages.

So-called "atomizer" type inhalers disperse liquid particles into an inhaled gas such as air. The inhaled medicine is carried within the liquid, for example the medicine may be in solution with the liquid. Such a delivery method can be suitable for certain medicines that are adequately stable in the liquid, for example medicines that can maintain efficacy in the liquid over long periods. However, many medicines are unsuitable for long term storage in liquid form.

So-called "dry powder" type inhalers are configured to disperse dry solid particles of a medicine into an inhaled gas. Dry powder inhalers have the advantage that the medicine is stored in dry solid form and therefore may retain its efficacy longer. However, the solid particles can be relatively large or irregular in size and shape, adversely affecting the uniformity and depth of drug distribution within the lungs and/or potentially irritating the lungs of the inhaling patient.

So-called "vaporizing" inhalers utilize a heat source to cause rapid sublimation, and/or melting followed by evaporation, of a solid medicine into gaseous form. An example of a vaporizing inhaler is described in U.S. Patent Publication No. 2005/0268911A1 to Cross et al. The patient typically inhales the heated medicinal gas after it is mixed with a cooler diluting gas such as air. Vaporizing inhalers have the advantage that the medicine is stored in solid form (i.e. potentially maintaining efficacy over a longer period of storage) and the inhaled gas is less likely to irritate the lungs of the inhaling patient because the inhaled gas does not include an excessive size or number of solid particles. However, because vaporizing inhalers typically require a rapid but well-controlled temperature rise in the solid medicine, the design of a practical, safe, and low-cost vaporizing inhalers can be a formidable challenge.

Thus, there is a need in the art for an improved vaporizing inhaler design that is suitable for safe and practical use while also being suitable for high-volume manufacture at acceptably low cost.

SUMMARY

A medicine vaporizer for an inhaler includes a metal louver. The metal louver has a first end and an opposing second end, and defines a louver thickness. The medicine vaporizer also includes first and second electrically conductive pins that define a pin thickness greater than the louver thickness. The first electrically conductive pin includes a first crimping region that is attached to and crimped over the first end. The second electrically conductive pin includes a second crimping region that is attached to and crimped over the second end.

BRIEF DESCRIPTION OF THE DRAWINGS

FIG. 3 is a perspective view of a single louver and pin sub-assembly, according to an exemplary embodiment of the present invention.

FIGS. 4A-C depict various stages of a louver and pin assembly process according to an exemplary embodiment of the present invention.

DESCRIPTION OF THE PREFERRED EMBODIMENTS

Figure 1:
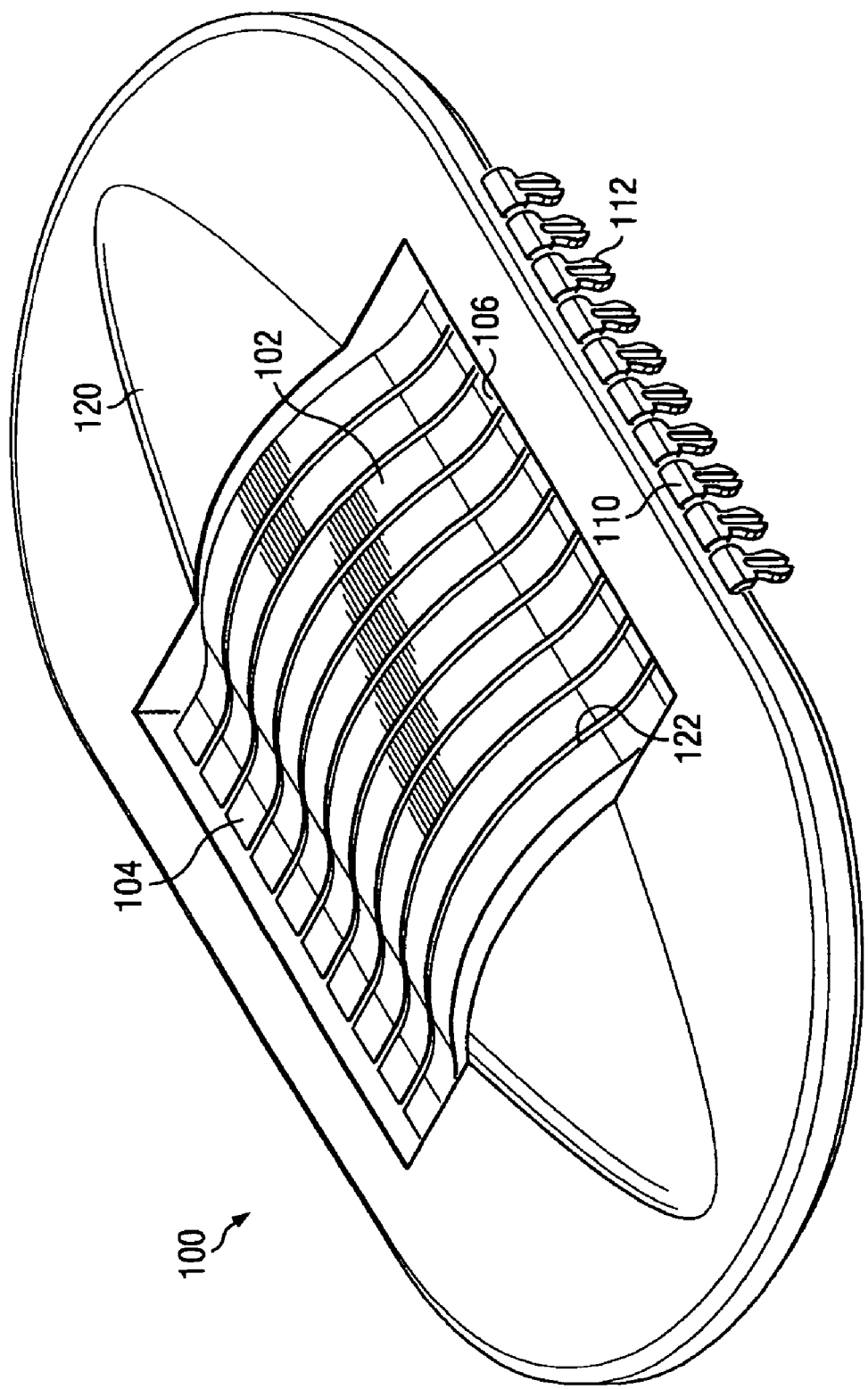
FIG. 1 is a perspective view of a medicine vaporizer capable of incorporating an embodiment of the present invention.

FIG. 1 is a perspective view of a medicine vaporizer 100 capable of incorporating an embodiment of the present invention. The medicine vaporizer 100 includes twenty-five metal louvers (e.g. metal louver 102), each defining a louver thickness. For example, each of the louvers may be fabricated from austenitic stainless steel, and may define a thickness is in the range 5 µM to 100 µM. Each of the metal louvers (e.g. 102) has a first end (e.g. 104) and an opposing second end (e.g. 106).

The medicine vaporizer 100 of FIG. 1 also includes fifty electrically conductive pins (e.g. 110). Each of the electrically conductive pins (e.g. 112) defines a pin thickness greater than the thickness of a corresponding metal louver (e.g. 102). Each of the electrically conductive pins (e.g. 112) includes a material that has a higher electrical conductivity than that of a corresponding metal louver (e.g. 102). For example, each of the electrically conductive pins (e.g. 110) may be fabricated from copper, and may define a pin thickness in the range 125 µm to 1.3 mm. As shown further in FIGS. 3 and 4, each of the electrically conductive pins (e.g. 112) includes a crimping region that is attached to and crimped over one of the ends (e.g. 106) of a corresponding metal louvers (e.g. 102).

The medicine vaporizer 100 of FIG. 1 also includes a frame 120 in contact with the fifty electrically conductive pins (e.g. 110). Preferably, the frame 120 is an injection molded plastic frame that partially encapsulates each of the electrically conductive pins. The frame 120 serves to hold and maintain the position and spatial orientation of the fifty electrically conductive pins (e.g. 110) relative to each other, so as to control the relative position and spatial orientation of the louvers (e.g. 102), including to maintain the relative spacing between the louvers (e.g. 102). The relative spacing between the louvers (e.g. 102) provides air gaps (e.g. 122) that ensure electrical isolation of each louver from another. The frame 120 also serves to maintain the spatial arrangement of the electrically conductive pins (e.g. 110) so that they can be aligned with a pattern of corresponding pin receptacles in a printed circuit board (not shown).

Figure 2:
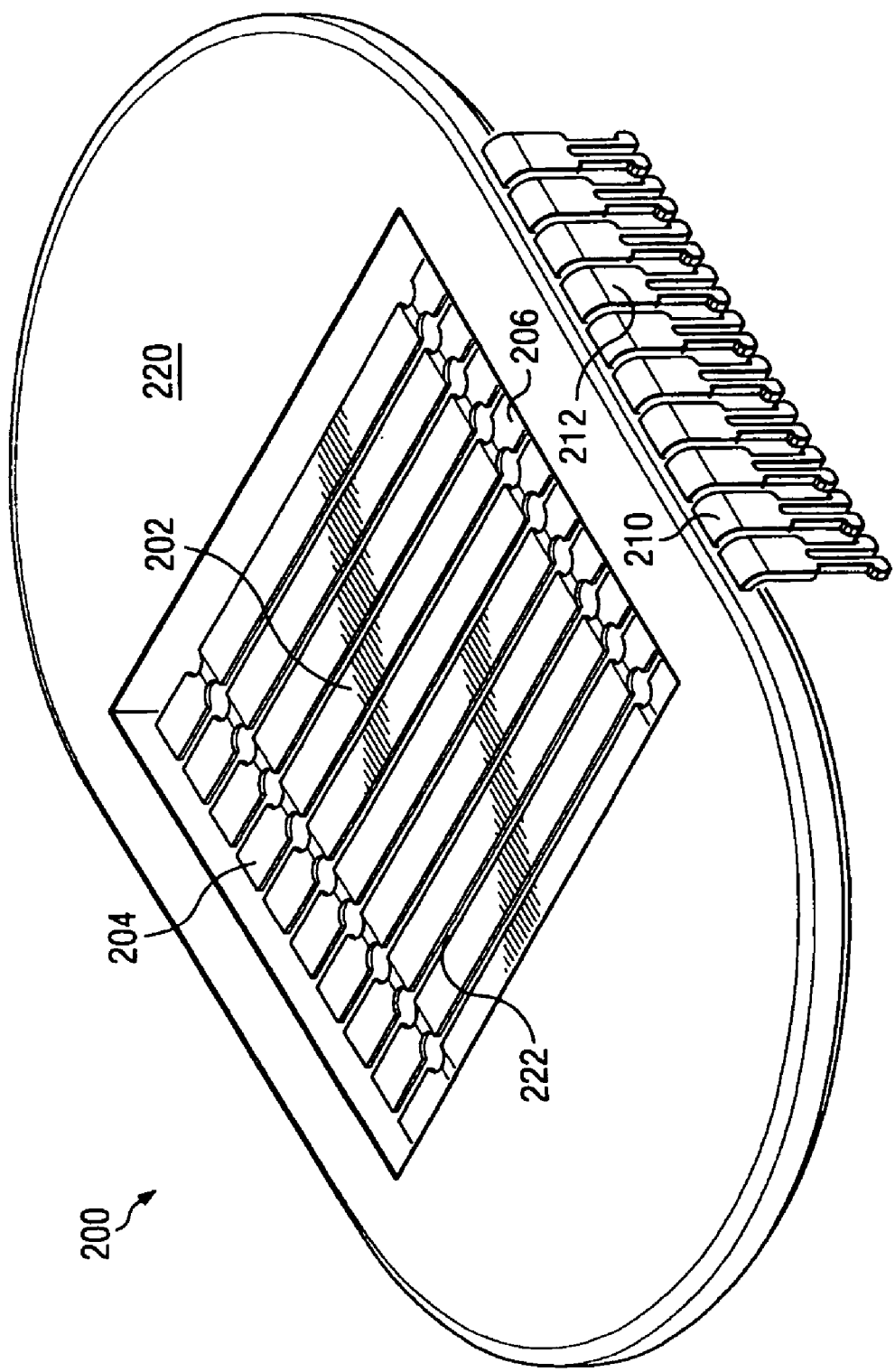
FIG. 2 is a perspective view of another medicine vaporizer capable of incorporating an embodiment of the present invention.

FIG. 2 is a perspective view of another medicine vaporizer 200 capable of incorporating an embodiment of the present invention. The medicine vaporizer 200 includes twenty-five metal louvers (e.g. metal louver 202), each defining a louver thickness. For example, each of the louvers may be fabricated from austenitic stainless steel, and may define a thickness is in the range 5 μm to 100 μm. Each of the metal louvers (e.g. 202) has a first end (e.g. 204) and an opposing second end (e.g. 206).

The medicine vaporizer 200 of FIG. 2 also includes fifty electrically conductive pins (e.g. 210). Each of the electrically conductive pins (e.g. 212) defines a pin thickness greater than the thickness of a corresponding metal louver (e.g. 202). Each of the electrically conductive pins (e.g. 212) includes a material that has a higher electrical conductivity than that of a corresponding metal louver (e.g. 202). For example, each of the electrically conductive pins (e.g. 210) may be fabricated from copper, and may define a pin thickness in the range 125 μm to 1.3 mm. As shown further in FIGS. 3 and 4, each of the electrically conductive pins (e.g. 212) includes a crimping region that is attached to and crimped over one of the ends (e.g. 206) of a corresponding metal louvers (e.g. 202).

The medicine vaporizer 200 of FIG. 2 also includes a frame 220 in contact with the fifty electrically conductive pins (e.g. 210). Preferably, the frame 220 is an injection molded plastic frame that partially encapsulates each of the electrically conductive pins. The frame 220 serves to hold and maintain the position and spatial orientation of the fifty electrically conductive pins (e.g. 210) relative to each other, so as to control the relative position and spatial orientation of the louvers (e.g. 202), including to maintain the relative spacing between the louvers (e.g. 202). The relative spacing between the louvers (e.g. 202) provides air gaps (e.g. 222) that ensure electrical isolation of each louver from another. The frame 220 also serves to maintain the spatial arrangement of the electrically conductive pins (e.g. 210) so that they can be aligned with a pattern of corresponding pin receptacles in a printed circuit board (not shown).

FIG. 3 is a perspective view of a single louver and pin sub-assembly 300, according to an exemplary embodiment of the present invention. The louver and pin sub-assembly 300 includes a metal louver 302 and two electrically conductive pins 310, 312. The metal louver 302 includes a first end 304 and an opposing second end 306 and at least one clean surface suitable for at least partial coating by a medicine. The first electrically conductive pin 310 includes a first crimping region 334 that is attached to and crimped over the first end 304, and the second electrically conductive pin 312 includes a second crimping region 336 that is attached to and crimped over the second end 306.

In the embodiment of FIG. 3, the first crimping region 334 and the first electrically conductive pin 310 are a single part having material continuity rather than being an assembly of sub-parts. Likewise, the second crimping region 336 and the second electrically conductive pin 312 are a single part having material continuity rather than being an assembly of sub-parts. However, it is contemplated that the first and second electrically conductive pins 310, 312 could each be an assembly of sub-parts. Moreover, the first crimping region 334 may have a material composition that is different from that of the first electrically conductive pin 310 outside of the crimping region. For example, the first crimping region 334 may include a crimping region surface that is plated with a dissimilar conductive plating material that later makes contact with the first end 304. The same could be true of the second crimping region 336 and the second end 306.

FIGS. 4A-C depict various stages of a louver and pin assembly process according to an exemplary embodiment of the present invention. FIG. 4A depicts an electrically conductive pin 400 that has been stamped from an electrically conductive sheet (e.g. a copper sheet), and then formed to include a crimping region 410. The crimping region 410 includes a horizontal land 420 and a vertical flap 430. In certain embodiments, the crimping region 410 is plated with a conductive plating material.

FIG. 4B additionally depicts a metal louver 440 that has been stamped from a metal sheet (e.g. a stainless steel sheet) having a thickness less than the electrically conductive sheet from which the pin 400 was stamped. In certain embodiments, the louver 440 is also coined to create a region of the louver 440 that is thinner than the sheet from which it was stamped. Such coining can optionally be accomplished at the same time as the stamping. An end 450 of the metal louver 440 shown in FIG. 4B has been positioned adjacent to the crimping region 410 of electrically conductive pin 400. Specifically, in the embodiment shown in FIG. 4B, the end 450 has positioned to rest upon horizontal land 420.

Next, as shown in FIG. 4C, a crimping force 460 is brought to bear upon the vertical flap 430 of the conductive pin 400, bending it over the end 450 of the metal louver 440. The crimping force 460 thusly crimps the crimping region 410 over the 450. In certain embodiments, the crimping region 410 is subsequently staked to enhance the connection between the metal louver 440 and the electrically conductive pin 400.

In an alternative embodiment the crimped connections are further improved by employing materials or material coatings that form metal-metal bonds across the crimp interface. Such a strategy can decrease the mean and/or variability of electrical resistance across the crimp connection. Metal-metal bonding may also improve the mechanical strength of the crimp connection.

Several methods can be used to obtain a metal-metal bond. One such method employs the use of a solder on the regions to be bonded. For example, a solder material can be plated to the surface of horizontal land 420 and/or a contacting surface of the metal louver 440 in FIG. 4. The plating can be done using well established methods including continuous and batch type processing, and may optionally use a mask to preclude solder plating on non-contact surfaces. The plating material may be selected from a wide range of compositions, for example 85% Sn, 15% Pb; pure Sn; 95.5% Sn, 4.0% Ag, 0.5% Cu, as well as other material compositions fabricated from In, Sb, Sn, Pb, Cu, and other elements. The plating thickness may range from 0.2 to 50 microns, with the optimum thickness dependant on the condition of the substrate surface and component level factors including fit. Following plating of the components, the assembly is crimped and subsequently heated to form the solder bond.

Solder materials can be remelted and reflowed after bonding. Other approaches can also be employed to affect a metal-metal bond, including metal combinations that allow transient liquid phase (TLP) bonding. Via diffusion at a single temperature, TLP bonding allows the formation of a liquid metal that wets the surfaces to be bonded and then solidifies. Unlike the use of solder, TLP bonds cannot be remelted or reflowed, but are generally more robust and may offer greater mechanical strength. When selecting materials for metal-to-metal bonding, one consideration is that the melting temperature of the material be low enough to facilitate bonding, yet high enough so that subsequent heating associated with use of the inhaler (i.e. medicinal sublimation) does not re-melt the metal-to-metal bond material.

For example, copper and stainless steel components may be TLP bonded after one or both interfacing surfaces are plated with a suitable bonding material (e.g. Mg, Au, Ag, Cu, Ni, Be, etc, and/or combination thereof). The plating methods are similar to those used for solder deposition. As an alternative to plating, a thin metal foil may be placed between bonding surfaces. Following metal deposition or placement, the junction is heated to induce the TLP mechanism.

Both solder bonding and TLP bonding can reduce variation in electrical resistance via the formation of a metal meniscus to bridge separations (if any) at the crimped interface, making the effective length of contact between the surfaces more repeatable.

Coating with a soft metal such as gold prior to crimping can also decrease the electrical resistance across the junction. The soft metal conforms to surface asperities and increases the effective contact area of mating surfaces. The resistance to corrosion offered by gold also improves the reliability of the junction. Other metals that can be used in this way include, but are not limited to, silver, platinum, indium, and various alloys.

Preferably, all of the electrically conductive pins used in the medicine vaporizer are formed at the same time to enhance the speed and economy of the medicinal vaporizer fabrication process. Also, the crimping regions of the two electrically conductive pins that are disposed adjacent the two ends of each louver are preferably crimped at the same time or in immediate sequence to more efficiently utilizes the period during which tools must hold the components in desired relative positions. In certain embodiments, attaching the metal louvers to the conductive pins by crimping, rather than by a prior art method, may reduce contamination and heating, and may render the medicine vaporizer fabrication more economical and better suitable for high volume manufacture.

Either before or after the crimping depicted in FIGS. 4A-C, a plastic frame may be injection molded to be in contact with the electrically conductive pins. For example, a plastic frame may be injection molded to partially encapsulate all of the electrically conductive pins. In certain embodiments, attaching the metal louvers to the conductive pins by crimping enables such attachment to be accomplished after molding the plastic frame. The crimping depicted in FIGS. 4A-C is preferably but not necessarily accomplished after molding the plastic frame so that the thinner and more delicate metal louvers are held with more stability after attachment to the conductive pins and are therefore better protected from subsequent handling damage during the remainder of the inhaler fabrication process.

In the foregoing specification, the invention is described with reference to specific exemplary embodiments thereof, but those skilled in the art will recognize that the invention is not limited thereto. It is contemplated that various features and aspects of the above-described invention may be used individually or jointly and possibly in an environment or application beyond those described herein. The specification and drawings are, accordingly, to be regarded as illustrative and exemplary rather than restrictive. The terms "comprising," "including," and "having," as used herein are intended to be read as open-ended terms.

We claim:

1. A medicine vaporizer for an inhaler, the medicine vaporizer comprising:
    at least one metal louver defining a louver thickness, the at least one metal louver having a first end and an opposing second end; and
    first and second electrically conductive pins, each defining a pin thickness greater than the louver thickness, the first electrically conductive pin including a first crimping region that is attached to and crimped over the first end, and the second electrically conductive pin including a second crimping region that is attached to and crimped over the second end;
    wherein the first crimping region includes a crimping region surface that is plated with a conductive plating material and the conductive plating material is in contact with the first end.

2. The medicine vaporizer of claim 1 wherein the first crimping region and the first electrically conductive pin are a single part having material continuity rather than being an assembly of sub-parts.

3. The medicine vaporizer of claim 1 wherein the first conductive pin is an assembly of sub-parts, the assembly including the first crimping region.

4. The medicine vaporizer of claim 3 wherein the first crimping region has a material composition that is different from that of the first electrically conductive pin outside of the crimping region.

5. The medicine vaporizer of claim 1 wherein the conductive plating material is selected from the group consisting of Sn, Ag, In, Sb, Pb, Au, Mg, Ni, Cu, and Be.

6. The medicine vaporizer of claim 1 wherein the conductive plating material forms a layer having a thickness in the range 0.2 to 50 microns.

7. The medicine vaporizer of claim 1 further comprising a metal-to-metal bond between the first crimping region and the first end.

8. The medicine vaporizer of claim 7 wherein the metal-to-metal bond includes a meniscus.

9. The medicine vaporizer of claim 1 wherein the first and second electrically conductive pins comprise a material that has a higher electrical conductivity than that of the at least one metal louver.

10. The medicine vaporizer of claim 1 wherein the at least one metal louver comprises austenitic stainless steel.

11. The medicine vaporizer of claim 1 wherein the louver thickness is in the range 5 μm to 100 μm.

12. The medicine vaporizer of claim 1 wherein the pin thickness is in the range 125 μm to 1.3 mm.

13. The medicine vaporizer of claim 1 wherein the at least one metal louver further comprises a clean surface suitable for at least partial coating by a medicine.

14. The medicine vaporizer of claim 1 further comprising a frame in contact with the first and second electrically conductive pins.

15. The medicine vaporizer of claim 14 wherein the frame is an injection molded plastic frame.

16. A medicine vaporizer for an inhaler, the medicine vaporizer comprising:
    a plurality of metal louvers, each defining a louver thickness, and each having a first end and an opposing second end; and
    a plurality of electrically conductive pins, each defining a pin thickness greater than the louver thickness, and each including a crimping region that is crimped over one of the plurality of metal louvers adjacent one of its two opposing ends;
    wherein the crimping region includes a crimping region surface that is plated with a conductive plating material and the conductive plating material is in contact with the one of the two opposing ends.

17. The medicine vaporizer of claim 16 wherein the crimping region and the electrically conductive pin that includes it are a single part having material continuity rather than being an assembly of sub-parts.

18. The medicine vaporizer of claim 16 wherein at least one of the plurality of electrically conductive pins is an assembly of sub-parts, the assembly including the crimping region.

19. The medicine vaporizer of claim 18 wherein the crimping region has a material composition that is different from a second region of the electrically conductive pin that includes the crimping region.

20. The medicine vaporizer of claim 16 wherein the conductive plating material is selected from the group consisting of Sn, Ag, In, Sb, Pb, Au, Mg, Ni, Cu, and Be.

21. The medicine vaporizer of claim 16 wherein the conductive plating material forms a layer having a thickness in the range 0.2 to 50 microns.

22. The medicine vaporizer of claim 16 wherein the louver thickness is in the range 5 μm to 100 μm.

23. The medicine vaporizer of claim 16 wherein the pin thickness is in the range 125 μm to 1.3 mm.

24. The medicine vaporizer of claim 16 further comprising a metal-to-metal bond between the crimping region and one of the plurality of metal louvers.

25. The medicine vaporizer of claim 24 wherein the metal-to-metal bond includes a meniscus.

26. The medicine vaporizer of claim 16 wherein the plurality of metal louvers further comprises a plurality of clean surfaces suitable for at least partial coating by a medicine.

27. The medicine vaporizer of claim 16 further comprising a frame in contact with the plurality of electrically conductive pins.

28. A method of fabricating a medicine vaporizer for an inhaler, the method comprising the acts of:
    stamping at least one metal louver from a first metal sheet having a first sheet thickness, the at least one metal louver having a first end and an opposing second end;
    stamping first and second electrically conductive pins from a second metal sheet having a second sheet thickness thicker than the first sheet thickness;
    forming the first electrically conductive pin to create a first crimping region dimensioned to accept the first end;
    forming the second electrically conductive pin to create a second crimping region dimensioned to accept the second end;
    positioning the at least one metal louver relative to the first and second electrically conductive pins such that a portion of the first end is disposed adjacent the first crimping region and such that a portion of the second end is disposed adjacent the second crimping region;
    crimping the first crimping region over the first end;
    crimping the second crimping region over the second end; and
    coining the at least one metal louver to include a louver region of reduced thickness that is thinner than the first sheet thickness.

29. The method of claim 28 wherein the act of forming the first electrically conductive pin is accomplished at the same time as the act of forming the second electrically conductive pin.

30. The method of claim 28 wherein the act of crimping the first crimping region is accomplished at the same time as the act of crimping the second crimping region.

31. The method of claim 28 wherein the act of stamping the at least one metal louver is accomplished at the same time as the act of coining the at least one metal louver.

32. The method of claim 28 wherein the second sheet comprises copper.

33. The method of claim 28 further comprising injection molding a plastic frame in contact with the first and second electrically conductive pins.

34. The method of claim 28 further comprising staking the first crimping region after it is crimped.

35. The method of claim 28 further comprising plating the first crimping region with a conductive plating material.

36. The method of claim 35 further comprising heating the conductive plating material sufficiently to temporarily change its phase from solid to liquid.

\* \* \* \* \*